US00PP08019P

United States Patent [19]

Moore

[11] Patent Number: Plant 8,019

[45] Date of Patent: Nov. 3, 1992

[54] ROSE PLANT NAMED 'MORSPRING'

[75] Inventor: Ralph S. Moore, Visalia, Calif.

[73] Assignee: Spring Hill Nurseries Company, Tipp City, Ohio

[21] Appl. No.: 695,433

[22] Filed: May 3, 1991

[51] Int. Cl.[5] ..... A01H 5/00

[52] U.S. Cl. ..... Plt./2

[58] Field of Search ..... Plt. 2, 6, 22, 28, 29, Plt./12, 13

*Primary Examiner*—Howard J. Locker

[57] ABSTRACT

This invention relates to a new and distinct variety of rose plant, primarily identified by its double flowers with the petals being generally striped red and white and the plant being of vigorous climbing habit.

1 Drawing Sheet

The present invention relates to a new and distinct variety of hardy, climbing rose plant of the Floribunda class; the variety being primarily characterized — as to novelty — by double flowers with the petals being striped red and white.

The variety is further characterized by:

An abundance of bloom, with flowers usually borne in small clusters of 3 to 5 (sometimes more).

Some fragrance.

A plant which is vigorous, of upright shape with large matte foliage with pointed leaflets; the buds and flowers being similar in form to Little Darling (Floribunda — U.S. Plant Pat. No. 1,581, expired) but with less petals.

The plant, which has a normal height of 8-10 feet can easily be trained on pillar, trellis or fence.

A plant which grows and blooms satisfactorily outdoors in the garden and provides excellent garden decoration as well as cut flowers.

The present variety of climbing Floribunda was originated by me at my nursery, located at Visalia, Calif., under conditions of careful control and observation, as a cross between Little Darling (U.S. Plant Pat. No. 1,581) as the seed parent and Ferdinand Pichard (hybrid perpetual — not patented) as the pollen parent.

Subsequent to origination of the variety I successfully asexually reproduced it at my nursery, located as aforesaid, by budding as well as by cuttings; the reproductions having run true in all respects.

The present variety differs from its parents:

(1) Little Darling — upright, bush, pink blend, no stripe.

(2) Ferdinand Pichard — upright (tall) plant (not climber) with striped flowers. Plant not as vigorous or branched as present variety nor as prolific in in flowering.

Growth habit of MORspring is similar to Paul's Scarlet Climber. Repeat flowering after the heavy spring bloom, blooming on ends of new growth throughout season.

The color photographs illustrate the variety including the foliage, buds and flowers.

Referring now specifically to the new and distinct variety of climbing rose plant, the following is a detailed description thereof in outline; all major color plate identifications being by reference to the British Colour Council Horitcultural Colour Chart, except where common terms of color definition are employed.

Type: Hardy; climbing, upright; seedling; outdoors; garden decoration.

Class: Floribunda (climbing).

*Variety identification.*—*MORspring.*

*Commercial synonym.*—*Climbing Peppermint Delight.*

Flowers borne: Several together in loose clusters on sturdy stems.

Quantity of bloom: Abundant.

Bud:

*Peduncle.*—Medium length; slender but sturdy; erect; medium green, sometimes tinted bronze. Nearly smooth or with some small hair-like apendages.

*Before calyx breaks.*—Size — medium. Form — ovoid to pointed, with several small foliaceous apendages on surface of bud; with foliaceous parts extending beyond the tip of the bud equal to one-half or more of its length. Color — medium green, occasionally tinted with bronze.

*As calyx breaks, color.*—Red or white, or blend of both.

*Opening.*—Opens well in all weather.

Sepals: Permanent; spear shaped; recurved.

Bloom:

*Size when fully open.*—Large, averaging about 8-9 cm (3½).

*Petalage.*—Double — averaging about 20-25 (or more) petals, arranged regularly plus (sometimes) several small petaloids.

*Form.*—Full, high centered — first becoming rounded with petals rolled loosely outward and downward. Open flowers show stamens.

Petals: Fairly thick; satiny on inside and on outside surface.

*Shape.*—Outside petals, broad lanceolate (wedge shaped) with rounded tip. Intermediate — broad lanceolate with nearly round or short acute tip. Inside — lanceolate with acute tip.

Color: Newly opened flower from a plant grown outdoors (May 1990) Visalia, Calif.:

*Outside petal.*—Inside surface — white or pale pink and striped (or variegated) with red (near Cherry 722/2 but often modified with white to give a different or lighter red color). Outside surface— similar, but with the red stripes less intense in color.

*Intermediate petal.*—Inside surface similar to outside petal. Outside surface similar to outside petal.

*Inner petal.*—Inside surface similar to intermediate petal: Outside surface — similar to intermediatre petal. NOTE: The color patterns and shades of red coloring vary so that no exact color identification (from color chart) can be made. The colors are essentially red and white.

*General color effect.*—Newly opened flowers — a kaleidoscope of red and white. Three days open — color — similar to fresh open flower, but less bright. Behavior — opens well in all weather. Spent petals or flowers drop off. Flower longevity (May-Jun. 1990) — 4-5 days or longer for individual flowers but flowers continue opening in the clusters over many days.

Reproduction organs:

*Stamens.*—Average number.

*Filament.*—Slender, yellow.

*Anthers.*—Well formed, yellow.

*Pollen.*—Abundant.

*Pistils.*—Average number.

*Styles.*—Short to medium length; reddish; bunched.

*Ovaries.*—All enclosed in calyx.

*Hips.*—Many; rounded; 1½-2 cm dia.; orange.

*Seed.*—Several in each hip.

Foliage:

*Leaves.*—Compound of five (sometimes three or seven) leaflets; large; leathery; matte.

*Leaflets.*—Shape: broad lanceolate; apex acute. Base — usually rounded. Color: medium green; near Spinach Green 0960 — or similar; new growth — normal (medium) green (sometimes tinted reddish). Rachis: medium strength; upperside may have a few very short hairs; grooved; underside may have several small thorns (or claws), otherwise quite smooth. Stipules: medium to long (up to 15 mm in length); medium width (up to 6 mm); short length — narrow points which turn out usually at about 45 degrees or more.

Growth:

*Habit.*—Upright; much branched.

*Growth.*—Vigorous.

*Canes.*—Strong; slender; sturdy; arching.

*Main stems.*—Color: medium green.

*Thorns.*—Average, of varying size and length — sharply hooked or curved downward. Thorns are frequently in pairs just below the leaf node.

*Hairs.*—Few or none.

The rose plant and its flowers are herein described may vary in slight detail due to climatic, soil and cultural conditions under which the variety may be grown; the present description being of the variety as grown at Visalia, Calif.

The following is claimed:

1. A new and distinct cultivar of climbing rose plant of the Floribunda class substantially as herein described and illustrated, said plant having a vigorous, upright and much branched habit, having buds and flowers which are variegated or striped in varying patterns of red and white, the bud being pointed in the early opening stage (resembling in form 'Little Darling', U.S. Plant Pat. No. 1,581), the flower being full (double) with many (20-25 or more) petals; and further characterized by the plant having repeat bloom, an abundance of large matte foliage, with main stems and shoots of average thorniness, said plant being easy to propagate from soft wood cuttings or by budding, and said plant bearing flowers in small clusters on medium length stems.

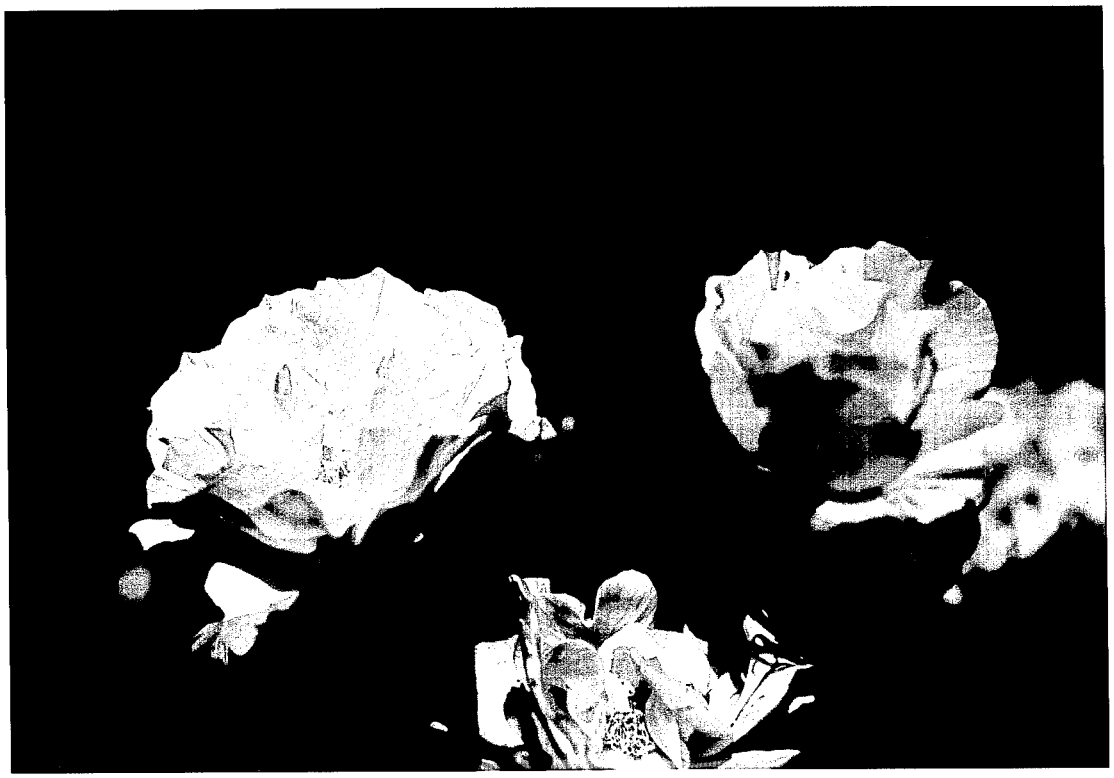
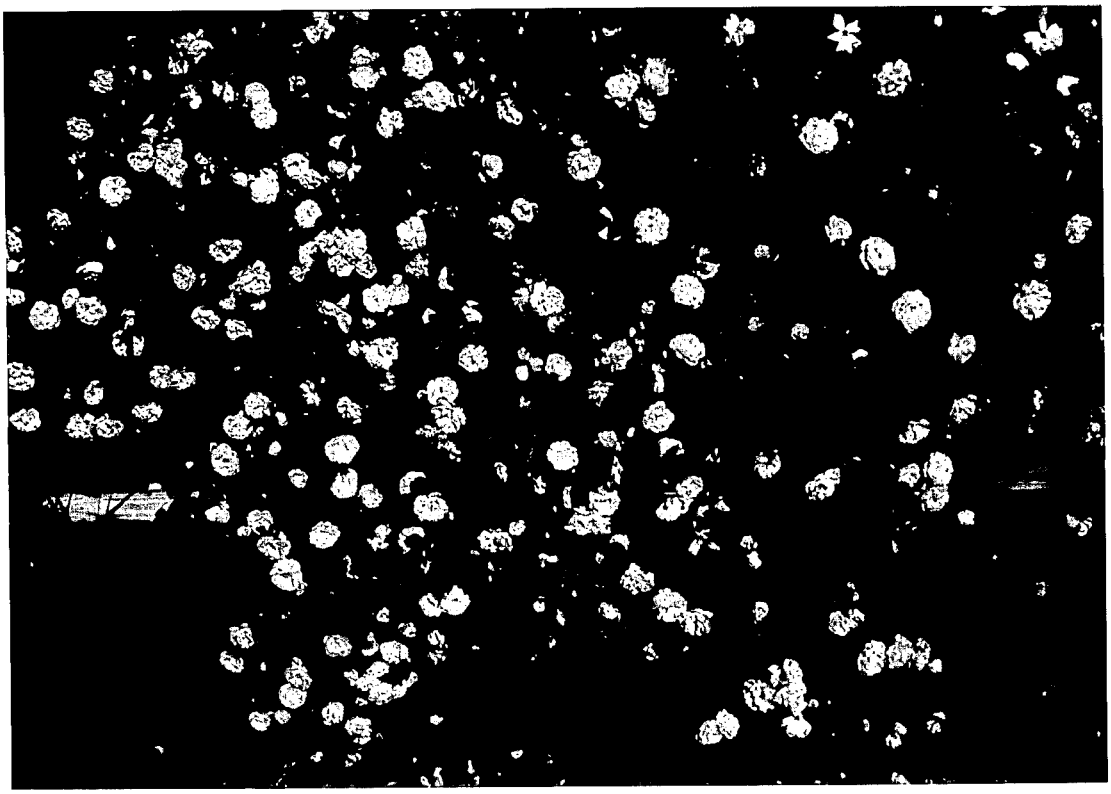

* * * * *